(12) United States Patent
Wilson (10) Patent No.: US 10,828,187 B2
(45) Date of Patent: Nov. 10, 2020

(54) ARM POSITIONING DEVICE FOR SUPPORTING THE ARMS OF A PATIENT IN AN ARMS-UP POSITION FOR THERAPEUTIC OR DIAGNOSTIC PURPOSES

(71) Applicant: Medtec, Inc., Orange City, IA (US)

(72) Inventor: Roger F. Wilson, Sarasota, FL (US)

(73) Assignee: MEDTEC, INC., Orange City, IA (US)

( * ) Notice: Subject to any disclaimer, the term of this patent is extended or adjusted under 35 U.S.C. 154(b) by 687 days.

(21) Appl. No.: 15/400,457

(22) Filed: Jan. 6, 2017

(65) Prior Publication Data

US 2017/0196724 A1     Jul. 13, 2017

Related U.S. Application Data

(60) Provisional application No. 62/276,365, filed on Jan. 8, 2016.

(51) Int. Cl.
    *A61G 15/00*      (2006.01)
    *A61F 5/37*      (2006.01)
    (Continued)

(52) U.S. Cl.
    CPC .......... *A61F 5/3761* (2013.01); *A61B 5/0555* (2013.01); *A61B 5/702* (2013.01);
    (Continued)

(58) Field of Classification Search
    CPC ........ A61F 5/37; A61F 5/3761; A61F 5/3769; A61F 5/01; A61B 5/0555; A61B 5/70;
    (Continued)

(56) References Cited

U.S. PATENT DOCUMENTS 3,476,256 A    11/1969   Anderson
4,730,801 A    3/1988   Cloward
(Continued)

FOREIGN PATENT DOCUMENTS

CN      201578765 U    9/2010
DE      202004003840 U1    7/2004
WO      2015144654 A1    10/2015

OTHER PUBLICATIONS

"Klarity Wing Board Radiotherapy Immobilization Device," Guangzhou Klarity Medical & Equipment Co., Ltd., <http://klarity2010.en.madeinchina.com/product/NSMQvbiKIIVY/ChinaKlarityWingBoardRadiotherapyImmobilizationDevice.html>, retrieved Dec. 29, 2015.

(Continued)

*Primary Examiner* — Victoria J Hicks
(74) *Attorney, Agent, or Firm* — Snyder, Clark, Lesch & Chung, LLP (57) ABSTRACT

An arm positioning device for supporting the arms of a patient in an arms-up position for some therapeutic or diagnostic procedure on the patient is disclosed. The device includes a base, a pair of wings or panels, and a pair of arm supports. The wings or panels extend upwardly and outwardly from the base and each mounts a respective one of the pair of arm supports thereon. The arm supports are configured to be slid along the wing or panel on which they are mounted to any one of plural working positions wherein they are located above the wing to hold the upper arm of a patient thereon. Each of the arm supports includes a cuff, which is pivotable to a retracted position located below the wing on which the arm support is mounted so as not to interfere with the placement of the patient on the arm positioning device.

16 Claims, 4 Drawing Sheets

(51) Int. Cl.
  *A61B 6/04* (2006.01)
  *A61B 5/055* (2006.01)
  *A61B 5/00* (2006.01)
  *A61G 13/12* (2006.01)
  *A61N 5/10* (2006.01)

(52) U.S. Cl.
  CPC .............. *A61B 6/04* (2013.01); *A61B 6/0421* (2013.01); *A61G 13/1235* (2013.01); *A61N 2005/1097* (2013.01)

(58) Field of Classification Search
  CPC ......... A61B 5/702; A61B 6/04; A61B 6/0407; A61B 6/0492; A61B 6/0421; A61B 6/0428; A61G 13/124; A61G 13/12; A61G 13/1235; A61G 13/126; A61G 13/128; A61G 13/1285; A61G 13/129; A61G 13/1295; A61G 7/075; A61G 7/065; A61G 7/0755; A61G 13/1245; A61G 13/1205; A61N 2005/1097
  USPC ........................................................ 128/845
  See application file for complete search history.

(56) References Cited

U.S. PATENT DOCUMENTS

| | | | |
|---|---|---|---|
| 4,836,523 A | 6/1989 | Englander | |
| 4,915,101 A | 4/1990 | Cuccia | |
| 5,000,168 A * | 3/1991 | Lipson | A61F 5/01 128/845 |
| 5,214,814 A | 6/1993 | Eremita et al. | |
| 5,385,536 A * | 1/1995 | Burkhead | A61F 5/3753 2/45 |
| 5,410,769 A | 5/1995 | Waterman | |
| 5,467,782 A | 11/1995 | Wiseman | |
| 5,537,702 A | 7/1996 | Brown-Milants et al. | |
| 5,742,962 A * | 4/1998 | Yoshino | A61B 6/0421 5/600 |
| 5,771,512 A | 6/1998 | Kurakake et al. | |
| 6,026,812 A * | 2/2000 | Lipson | A61F 5/0585 128/882 |
| 6,663,055 B2 | 12/2003 | Boucher et al. | |
| 6,925,668 B2 | 8/2005 | Cuschieri et al. | |
| 7,017,209 B1 | 3/2006 | De Jong et al. | |
| 7,063,461 B2 | 6/2006 | Coppens et al. | |
| 7,555,794 B2 | 7/2009 | Zelnik et al. | |
| 7,597,477 B1 | 10/2009 | Hosseinian et al. | |
| 7,603,730 B2 | 10/2009 | Zelnik | |
| 7,673,836 B2 | 3/2010 | Wallock et al. | |
| 7,676,869 B2 | 3/2010 | Zelnik et al. | |
| 7,934,687 B2 * | 5/2011 | Crook | A61F 5/3761 128/845 |
| 8,156,587 B2 | 4/2012 | Gagneur et al. | |
| 8,374,312 B2 | 2/2013 | Mansfield | |
| 2004/0059268 A1 * | 3/2004 | Polonchek | A61G 7/0755 601/33 |
| 2004/0123389 A1 | 7/2004 | Boucher et al. | |
| 2004/0143295 A1 * | 7/2004 | Ponder | A61G 13/009 606/237 |
| 2005/0015879 A1 | 1/2005 | Cuschieri et al. | |
| 2008/0172791 A1 | 7/2008 | Walczyk | |
| 2012/0011653 A1 | 1/2012 | Coppens et al. | |
| 2015/0101619 A1 * | 4/2015 | Lassetter | A61F 5/3769 128/879 |

OTHER PUBLICATIONS

"Positioning & Immobilization Products," Radiation Products Design, Inc., www.rpdinc.com, 46 pages.
Meeks, Sanford, "Immobilization from rigid to non-rigid," Orlando Health, MD Anderson Cancer Center, Aug. 5, 2011, 56 pages.
"Wing Boards," CIVCO Medical Solutions, <http://www.civco.com/ro/breastpositioning/breastboards/extendedwingboardB7.htm>, retrieved Dec. 29, 2015.

\* cited by examiner

ARM POSITIONING DEVICE FOR SUPPORTING THE ARMS OF A PATIENT IN AN ARMS-UP POSITION FOR THERAPEUTIC OR DIAGNOSTIC PURPOSES

CROSS-REFERENCE TO RELATED APPLICATION

This application claims priority under 35 U.S.C. § 119 based on U.S. Provisional Patent Application No. 62/276,365 filed Jan. 8, 2016, the disclosure of which is incorporated by reference herein.

BACKGROUND

This invention relates generally to medical devices and more particularly devices for positioning and supporting the arms of a patient disposed on a patient support panel or couch-top for therapeutic or diagnostic purposes.

As is known wing-boards, also known as butterfly boards, are arm positioning devices for which are commonly used for positioning supporting the arms of a patient during treatment procedures of the breast, lung and thorax. Such devices are typically configured so that they can also be used within a CT scanner for diagnostic purposes. In either case, such devices are arranged to be disposed on a patient support panel, couch-top, or other conventional patient supports (e.g., a supine breast-board device) on which a supine patient is disposed adjacent the apparatus for performing the therapeutic or diagnostic procedure. Typically, such devices are in the form of an integral unit, sometimes called a Wing Board or a Butterfly Board, having a base from which a pair of panels or wings project upwardly and outwardly. The panels or wings serve to support the arms of the patient over the patient's head (commonly called the "arms up" position) when the patient's head and neck is disposed over the base of the device for treatment or diagnosis of the breast, lung, thorax or any other portion of the upper torso of the patient. To that end, the patient's head is typically disposed on a pillow or cushion located on the base of the device while his/her arms are held in the arms-up position. In the interest of comfort and assistance in the maintenance of a stable position handle or hand grip may be provided mounted on the base of the device or mounted on the patient support panel above the patient's head so that the handle can be grasped by the patient to enable the patient to hold his/her arms in the arms up position on the panels or wings during the treatment or diagnostic procedure. Particularly suitable arm positioning devices are available from Civco Medical Products, Inc. (hereinafter "CIVCO"), the assignee of this invention, under the trademarks Wing Board and Monarch. The CIVCO Wing Board device and the CIVCO Monarch device are made from durable, lightweight ABS. CIVCO also provides handles which are either of a U shape, a T shape and a M shape and which are arranged to be mounted on the CIVCO devices to enable a patient to grasp the handle to help support his/her arms on the wings or panels in the arms-up position.

Other vendors, such as Klarity Medical and Equipment Company, Bionix Radiation Therapy, provide wing-boards, butterfly boards or similar arm positioning devices.

While the aforementioned prior art arm positioning devices are generally suitable for their intended purposes, they nevertheless leave much to be desired from various standpoints, such as ease of use, adjustability, and comfort for the patient.

Thus, a need exists for an arm positioning device which addresses the shortcomings of the prior art. The subject invention does that by providing an arm positioning device having a pair wings on which are mounted respective adjustable arm supports. The arm supports can be readily moved from a retracted position to a working position and vice versa. When in the retracted position, the arm supports are located below the wings of the device so that they don't interfere with the placement of the patient on the device. When in the working position they are located above the wings or panel to comfortably support the arms of the patient in an arms-up position on the wings or panels without requiring any handles or hand grips for the patient to grasp onto to hold his/her arms in that position.

All references cited and/or identified herein are specifically incorporated by reference herein.

SUMMARY OF THE INVENTION

In accordance with one aspect of this invention an arm positioning device for supporting the arms of a patient is provided. The device comprises a base, a pair of wings or panels, and a pair of arm supports. The base is configured to be disposed on a support adjacent a diagnostic or therapy device for supporting the head and neck of a patient thereon. The wings or panels are secured to the base and extend upwardly and outwardly of from the base on either side thereof, each of the wings or panels mounts a respective one of the pair of arm supports thereon. Each of the arm supports is configured to be moved to working position located above the wing or panel on which the arm support is mounted to hold the upper arm of a patient thereon, whereupon the patient's arms are above the patient's head.

In accordance with one preferred aspect of this invention the base of the device includes a longitudinal axis, wherein the pair of wings or panels extends along the longitudinal axis, and wherein each of the arm supports is slidable with respect to the wing or panel on which it is mounted to any one of a plurality of positions along the longitudinal axis.

In accordance with another preferred aspect of this invention each of the arm supports are also movable to a retracted position located below the wing or panel on which the arm support is mounted so as not to interfere with the placement of the patient on the device.

In accordance with another preferred aspect of this invention each of the arm supports is pivotably mounted with respect to the wing or panel on which it is mounted so that the arm support can be pivoted between the working position and the retracted position and vice versa.

In accordance with another preferred aspect of this invention the device additionally comprises a pair of releasable locking mechanism, each configured for releasably locking a respective one of the pair of arm supports in any desired one of the plurality of positions along the longitudinal axis.

In accordance with another preferred aspect of this invention each of the arm supports comprises a cuff configured for receipt of the upper arm of the patient.

In accordance with another preferred aspect of this invention each of the cuffs is mounted on an extending portion of the arm support for pivotable movement with respect to the extending portion.

DETAILED DESCRIPTION OF THE PREFERRED EMBODIMENTS

Figure 1:
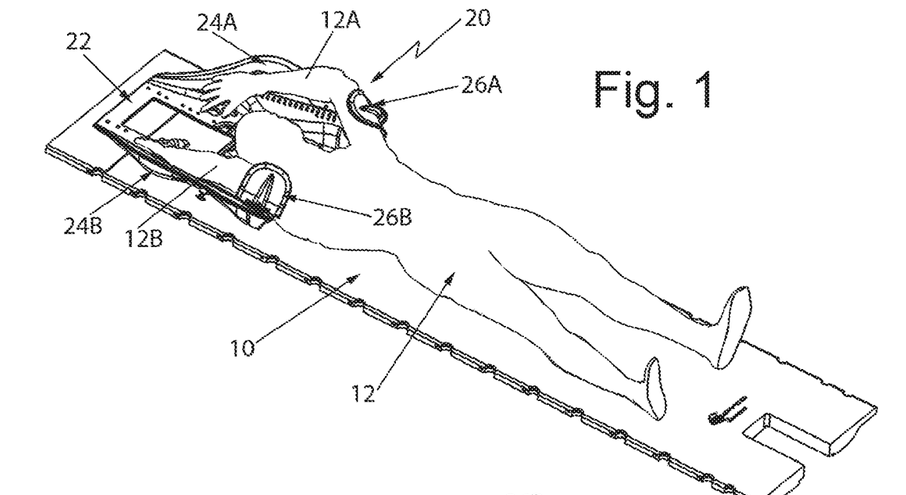
FIG. 1 is an isometric view of one exemplary embodiment of an exemplary arm positioning device including a pair of pair adjustable arm supports constructed in accordance with this invention shown disposed on a conventional couch top supporting a patient, wherein the adjustable arm supports are oriented in a working position to enable the patient to comfortably hold his/her arms over his/her head for therapeutic or diagnostic purposes.

Referring now to the various figures of the drawing wherein like reference characters refer to like parts, there is shown in FIG. 1 one exemplary embodiment of arm positioning device 20 constructed in accordance with this invention. The device 20 is configured to be mounted or otherwise disposed on a patient support panel, e.g., a couch-top, 10 on which a patient 12 is disposed in a supine position. The patient support panel 10 is itself disposed on a support, such as a pedestal of a therapy or diagnostic apparatus, e.g., a LINAC apparatus, a CT scanner, an MRI apparatus, etc. The arm positioning device 20 is particularly configured to comfortably support the arms 12A of the patient without stress to the patient above the patient's head in the arms-up position as shown in FIGS. 2 and 3, without requiring the patient to maintain muscle tension in the shoulders and use his/her hands to hold onto or grasp a hand-grip or handle, as has characterized prior art wing board like devices.

Figure 3:
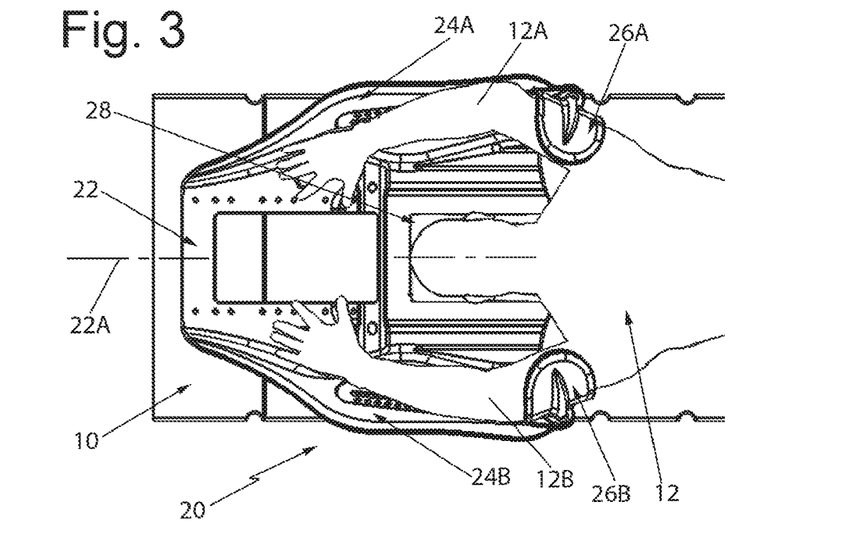
FIG. 3 is a top plan view of the arm positioning device shown in FIG. 1.
Figure 4:
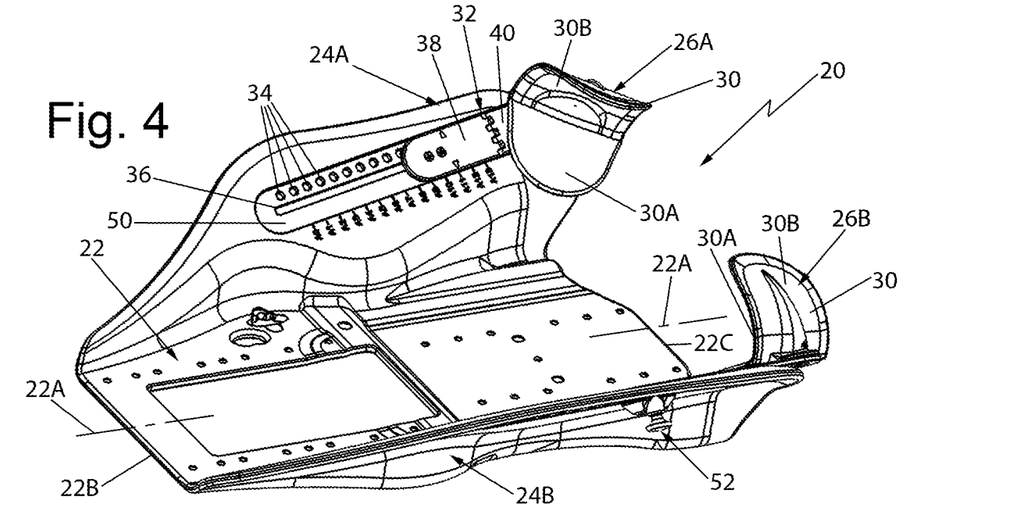
FIG. 4 is an enlarged isometric view of the arm positioning device shown in FIG. 1.

The device 20 is best seen in FIG. 4 and comprises a base 22, a pair of side panels or "wings" 24A and 24B, and a pair of arm supports 26A and 26B. Consistent with embodiments described herein, the wings 24A and 24B are secured to the base 22 in any suitable manner, such as frictionally, via fastening devices, or as an integrally formed unit. In the embodiment illustrated in FIG. 4, the base 22 and the wings 24A and 24B are formed as an integral unit, which can be formed of any suitable material, e.g., lightweight ABS. The base 22 is a generally planar, elongated rectangularly shaped member having a central longitudinal axis 22A, a top end 22B and a bottom end 22C. The upper surface of the base adjacent the bottom end 22C is configured to have a conventional head-supporting pillow or pad 28 (FIG. 3) disposed thereon. The pillow or pad 28 is arranged to receive the neck and back portion of the supine patient's head. Each of the wings 24A and 24B extends upwardly and outwardly from respective sides the base, flaring from the top end 22B toward the bottom end 22C, and include a front planar surface 25 and a rear planar surface 27.

The arm support 26A is configured to receive a portion, e.g., the triceps region, of the patient's left upper arm 12A, while the arm support 26B is configured to receive a that portion of the patient's right upper arm 12B. To that end, each of the arm supports 26A and 26B comprises an assembly of a cuff 30 and a mounting bracket 32. Each cuff may be shaped to comfortably receive the triceps region of a respective arm of the patient, while the bracket 32 serves to mount the cuff on the associated wing or panel of the base at any desired longitudinal position to comfortably support the patient's arm in the arms-up position. In particular, the bracket 32 slidably mounts the cuff 30 of the arm support 26A on the wing 24A, so that the cuff can be moved independently to any desired longitudinal positions along the axis 22A. Similarly, the bracket 32 slidably mounts the cuff 30 of the arm support 26B on the wing 24B, so that the cuff can be moved independently to any desired longitudinal positions along the axis 22A. In various embodiments, positioning of the arm supports 26A and 26B relative to the wings 24A and 24B, respectively, may enable either discrete or infinite placement. For example, in some embodiments (not shown), arm supports 26A and 26B may be moved to any of an infinite number of longitudinal positions relative to wings 24A and 2B and clamped or otherwise secured into place. In other embodiments, a finite number of discrete longitudinal positions may be supported. For example, as shown in FIG. 4, the discrete longitudinal positions are established by a plurality of holes 34 in each of the wings 24A and 24B.

Figure 2:
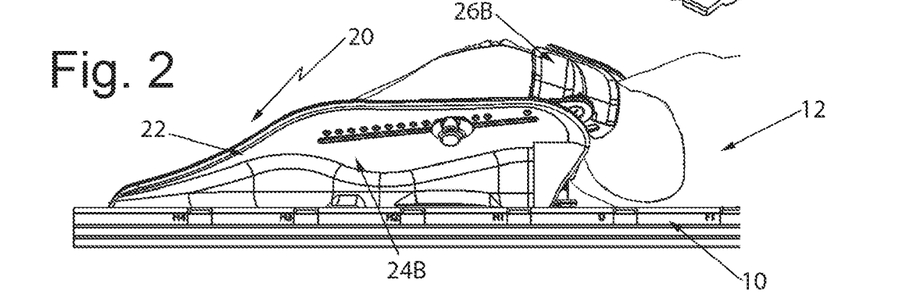
FIG. 2 is a side elevation view of the arm positioning device shown in FIG. 1.
Figures 7, 8:
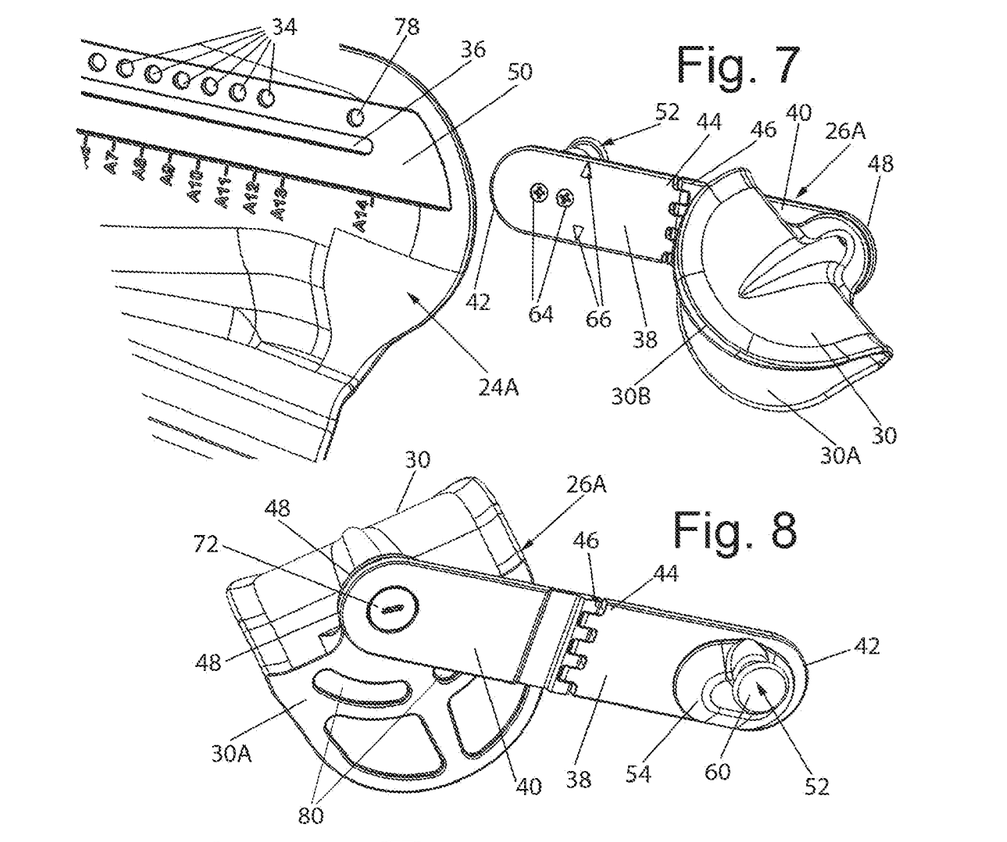
FIG. 7 is an exploded isometric view showing a portion of the arm positioning device and one of the adjustable arm supports of the arm positioning device shown in FIG. 1.
FIG. 8 is a somewhat enlarged isometric view of the arm support shown in FIG. 7, but taken from an oblique angle below the arm support.

As best seen in FIGS. 2, 4 and 7, the holes 34 of each wing are equidistantly spaced along a linearly extending slot 36 in that wing. Moreover, each slot 36 is angled slightly downward from its end located adjacent the bottom end 22C of the base 22 toward the top end 22B of the base, with the slot 36 terminating slightly past the midsection of the base.

Figure 9:
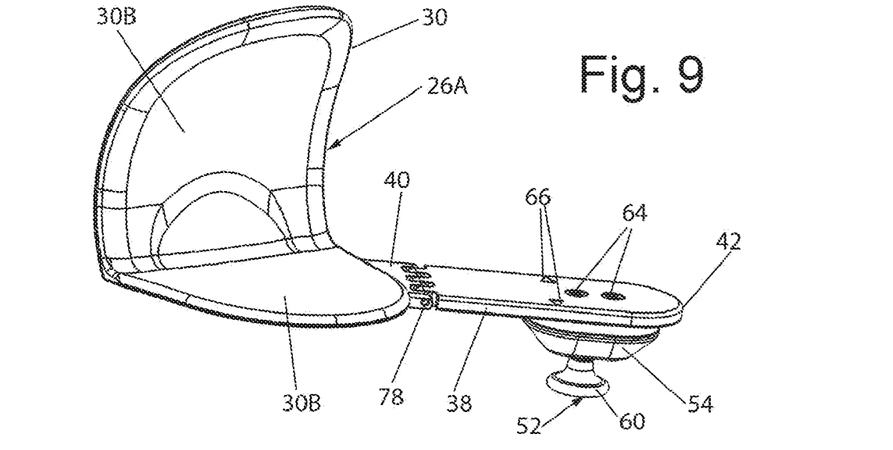
FIG. 9 is an isometric view similar to FIG. 8, but taken from an oblique angle above the arm support.

Each bracket 32 comprises a base member 38 and an extension member 40. The base member 38 is best seen in FIGS. 7-9 and comprises a generally planar member having a curved front edge 42 and a linear rear edge 44. The extension member 40 is also best seen in FIGS. 2, 4 and 7 and comprises a generally planar member having a linear front edge 46 and a curved rear edge 48. The front edge 46 of the extension member is pivotably connected to the rear edge 44 of the base member by a hinge pin 78 (FIG. 9). The base member 38 and the extension member of the arm support 26A are configured to be slidably received as a unit within a shallow channel or track 50 located in the upper surface of the wing 24A when those members are oriented so that they are coplanar (as will be described later). Similarly, the base member 38 and the extension member of the arm support 26B are configured to be slidably received as a unit within a shallow channel or track 50 located in the upper surface of the wing 24B when those members are oriented so that they are coplanar (as will be described later). The width of the channel or track 50 of the wing member 24A is just slightly wider than the width of the base member 38 and the pivotably connected extension member 40 of the arm support 26A. Similarly, the width of the channel or track 50 of the wing member 24B is just slightly wider than the width of the base member 38 and the pivotably connected extension member 40 of the arm support 26B. The slot 36 of the wing 24A extends within center of the channel or track 50 of that wing with the series of holes 34 of that wing also extending within that channel or track. Similarly, the slot 36 of the wing 24B extends within center of the channel or track 50 of that wing with the series of holes 34 of that wing also extending within that channel or track.

To hold the arm support 26A in any one of the discrete longitudinal positions along the slot 36 of the wing 24A, the arm support 26A also includes a releasable locking mechanism 52. The arm support 26B also includes a releasably locking mechanism 52 for holding it in in any one of the discrete longitudinal positions along the slot 36 of the wing 24B. The locking mechanisms 52 of both arm supports are of identical construction. Thus, in the interest of brevity only the locking mechanism 52 of arm support 26A will be described in detail. That locking mechanism 52 is mounted on the undersurface of the wing 24A and includes a member (to be described shortly) which is located within and extends through the slot 36 to fixedly secure the locking mechanism 52 to the base member 38.

Figure 10:
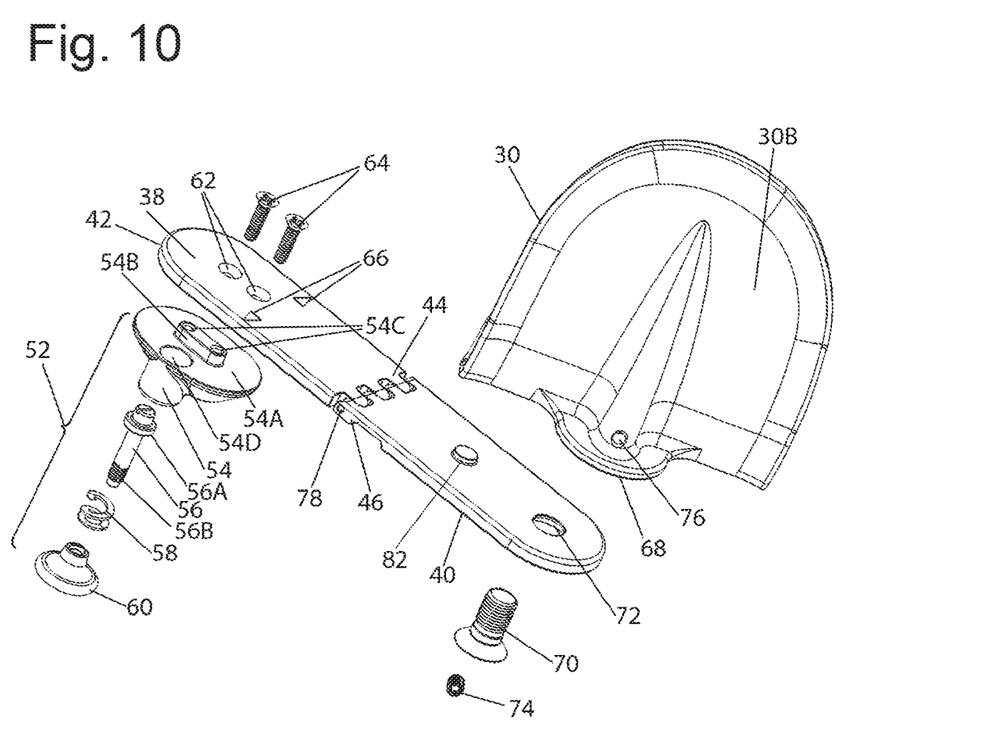
FIG. 10 is an enlarged exploded isometric view of the various components making up the arm support shown in FIGS. 8 and 9.

The releasable locking mechanism 52 is best seen in FIG. 10 and comprises a flanged base 54, a plunger pin 56, a helical spring 58, and a knob or cap 60. The undersurface 54A of the flanged base 54 of the releasable locking mechanism is planar and is configured to engage the undersurface of the wing 24A adjacent the slot 36. An elongated mesa-like member 54B projects outward from the planar surface 54A and is configured to be located within the slot 36. The base member 38 includes a pair of holes 62 through which a pair of screws 64 extends for threaded receipt in respective threaded holes 54C in the mesa-like member 54B. This arrangement fixedly secures the releasable locking mechanism 52, which is located on the undersurface of the wing 24A, to the base member 38 which is located on the upper surface of that wing. The flanged base 54 of the locking mechanism 52 includes a passageway 54D extending through it. The passageway 54D terminates at the bottom at the planar bottom surface 54A. The plunger pin 56 is located within the passageway 54D and is biased by the spring 58 so that the free end of the plunger pin normally extends out of the passageway 54D to project beyond the bottom surface of 54A. As such it can enter into any of the holes 34. The biasing of the plunger pin is achieved by providing it with an annular flange 56A located adjacent its free end. The spring 58 is a helical compression spring and is disposed on the plunger pin so that the spring 58 is interposed and compressed between the flange 56A and an undercut portion of the passageway 54D in the flanged base 54. This arrangement biases the free end of the plunger pin out of passageway 54D beyond the planar surface 54A. The opposite end of the plunger pin is threaded at 56B and normally extends out of the undercut portion of the passageway 54D opposite the planar surface 54A. The knob or cap 60 is threadedly secured to the extending threaded end 56B of the plunger pin. Thus, when one pulls outward on the knob or cap 60, that action overcomes the bias of the spring 56 to draw the free end of the plunger pin inward so that it doesn't extend beyond the planar surface 54A, thereby releasing the locking mechanism 52.

To move either arm support 24A or 24B to a desired longitudinal position along its associated wing, all that is required is for one to pull on the knob or cap 60 of that arm support against the bias of the spring 58, whereupon the free end of the plunger pin will be moved out of the hole in the wing in which it had previously been located. With the free end of the pin extended out of the hole in the wing the arm support can be slid down the slot 36 and the track 50 to a desired position therealong. Then the knob or cap released to enable the spring 58 to carry the free end of the pin 56 into the hole 34 at that desired position to thereby releasably lock the arm support in that longitudinal position.

As best seen in FIG. 7 plurality of alphanumeric indicia, i.e., "A1", "A2", "A3", "A4", "A5", "A6", "A7", "A8", "A9", "A10", "A11", "A12", and "A13", are located adjacent respective ones of the holes 34 on the wings 24A and 24B. The base member 38 of the arm support 24A includes a pair of indicators, e.g., arrowheads 66, adjacent each long edge of the base member. When the arm support 26A is moved to any one of the discrete longitudinal positions established by a desired one of the holes 34, the indicator arrowheads 66 will be aligned with one of the indicia "A1" to "A13". Thus, the alignment of the arrowheads with a particular one of the indicia "A1" to "A13" provides a visual indication of the precise longitudinal positioning of the arm support. This feature enables a user to readily set or reset the arm support to a precise position for the patient each time that the arm support is to be used with that patient.

Figure 5:
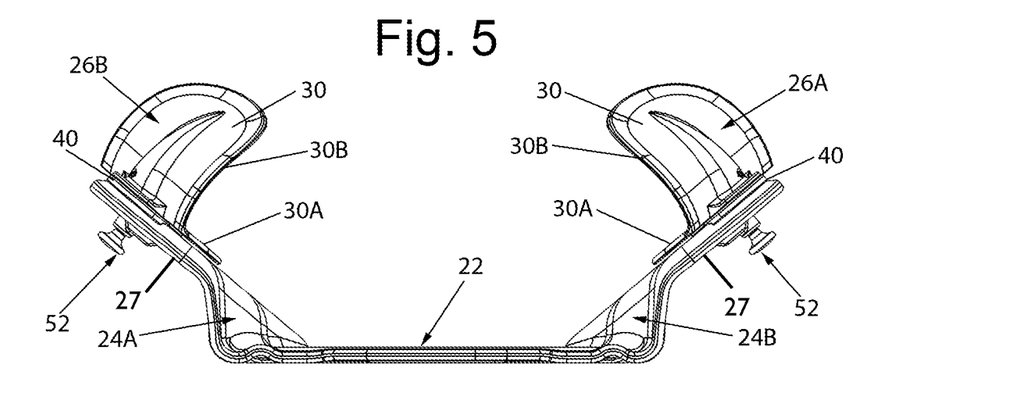
FIG. 5 is an end elevation view of the wing-board device shown in FIG. 4.
Figure 6:
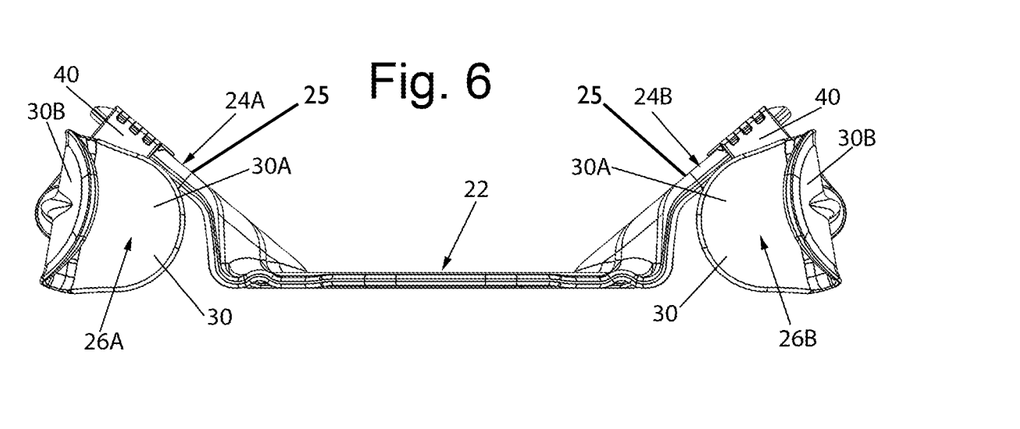
FIG. 6 is an end elevation view, similar to FIG. 5, but showing the pair of arm supports oriented in their retracted position.

Turning now to FIGS. 4-7 and 10, the details of each cuff 30 and the manner in which it is mounted on the extension member 40 of its arm support will now be discussed. It should be noted that the cuffs 30 of the arm support 26A and 26B are of identical construction. Thus, in the interest of brevity only the cuff 30 and the manner of its mounting on the extension member 40 of the arm support 26A will be described in detail. In particular, as best seen in FIGS. 4 and 5 the cuff 30 is a concave member having a generally planar section 30A and a curved section 30B. The sections 30A and 30B are preferably an integral unit, and can be formed of any suitable material, e.g., lightweight ABS.

As best seen in FIGS. 9 and 10, the planar section 30A of the cuff 30 is disposed on the top surface of the extension member 40 and is rotatably mounted with respect thereto. In particular, the curved section 30B includes a bracket portion 68 that projects outwardly from the outer surface of the curved section 30B and is located immediately adjacent the point at which the planar section 30A merges with the curved section 30B. A threaded hole (not shown) is located within the bracket portion 68. A screw 70 extends through a hole 72 in the extension member 40 for threaded engagement within the threaded hole in the bracket portions 68. Thus, the cuff is enabled to be pivoted or rotated through an arc about the central longitudinal axis of the screw 70 to thereby adjust the angular orientation of the cuff on the extension member 40. A set screw 74 is provided extending through a threaded hole 76 in the bracket portion 60 to adjust the degree of looseness of the pivotable mounting of the cuff on the extension member.

As best seen in FIG. 8, a pair of arcuate slots 80 is located in the planar section 30A of the cuff 30 on each side of the centerline of the section 30A. The slots 80 are mirror images of each other and are configured to receive a boss 82 (FIG. 10) projecting outward from the extension member 38 during the assembly of the arm positioning device 20. In particular, an appropriate one of the slots of the arm support 26A is chosen to receive the boss of the extension member of that arm support to keep the cuff of that support somewhat oriented properly for receiving the left arm 12A of the patient. Similarly, an appropriate one of the slots of the arm support 26B is chosen to receive the boss of the extension member of that arm support to keep the cuff of that support somewhat oriented properly for receiving the right arm 12A of the patient. By so doing so each arm support can be used on either wing or panel. Thus, there is no need for an arm support specifically tailored for the right arm of the patient and an arm support specifically tailored for the left arm of the patient. One arm support can be used for either arm of the patient by selecting the appropriate curved slot 80 for receipt of the boss 82.

Each extension member 40 is configured to be pivoted with respect to its associated base member 38 between an operative or working position located above front planar surface 25 and a retracted or storage position located below rear planar surface 27, and vice versa. When the extension member 40 of each arm support is in its operative or working position, it is coplanar with the base member 38, such that each arm support can be readily slid down the track 50 to a desired longitudinal position. When each arm support is slid along the track to the end of the track closest to the end 22C of the base, the extension member 40 of that arm support can be pivoted downward with respect to its base member to its retracted or storage position as shown clearly in FIG. 6. In that retracted or storage position the cuff 30 of the arm support will be located below the wing on which it is mounted. This enables the patient to be easily placed on the arm positioning device 20 with his her/head on the support pillow or pad 28 without interference of the cuff.

As best seen in FIG. 7 each track 50 includes an additional hole 78 within the track 50 and located closely adjacent the end of the slot 36 closest to the end 22A of the base member. Each hole 78 is used by its associated releasable locking mechanism 52 to hold the associated arm support in the retracted position. In particular, each hole 78 is configured to receive the pin 56 of the associated releasable locking mechanism 52 when the base member 38 is located at the end of the track 50. As such the extension member 40 can be pivoted downward to the retracted position carrying the cuff 30 below the associated wing. Each wing includes indicia, e.g., the alphanumeric "A14", located adjacent the hole 78. Thus, when each arm support is slid to the position at which its extension member can be pivoted downward to move the cuff to the retracted position, that position will be readily visible by virtue of the indicator arrowhead 66 aligning with the indicia A14.

With the cuffs in the retracted position or storage position, the arm position device is ready for use to receive the patient. To that end, once the patient is in the desired supine position on the couch-top 10 such that his/her head is on the pillow or pad 28 on the base of the arm positioning device, the patient can then move his/her arms to a comfortable arms-up position on the wings 24A and 24B. The extension members 40 of the two arm supports 26A and 26B can then be pivoted to their working position wherein they are coplanar with their associated base members 38. The arm supports 24A and 24B can then be slid to any desired longitudinal position by pulling the knob 60 of each of the releasably locking mechanisms 52 to draw its associated pin 56 out of the hole 78 and then sliding the arm support down the track 50 to the desired position so that the cuffs can receive the triceps region of the patient's arms. The cuffs 30 can be rotated about screws 72 to any desired orientation to most comfortably receive those portions of the patient's arms, with the boss 82 sliding in the curved slot 80 in which it is located. Once the arm supports are in the desired position holding the patient's arms in a comfortable arm-up position, the arm supports can be locked in place at that position by the releasably locking mechanisms, i.e., extending the pins 56 of those locking mechanisms into the hole 34 in the wings 24A and 24B with which they are aligned.

As should be appreciated by those skilled in the art the exemplary device 20 described above is merely one example of a multitude of devices that can be constructed in accordance with this invention, providing that the device includes a pair of arm supports each of which is mounted on an associated wing or projecting panel and which are configured to be moved to working position located above the wing on which the arm support is mounted to hold the upper arm of a patient thereon, whereupon the patient's arms are above the patient's head, and with each of the arm supports also being movable to a retracted or storage position located below the wing on which the arm support is mounted. Moreover, while the subject invention enables a patient to comfortably hold his/her arms in an arms-up position without requiring any other structure, e.g., a handle or hand grip, for the patient to grasp or grip while his/her arms are in that position, it is contemplated that the use of such handles or hand grips can be used, if desired. To that end, the base portion 22 of the device 20 may be provided with various mounting holes, like shown in FIGS. 3 and 4, for mount a handle or hand grip thereon.

The foregoing description of embodiments provides illustration, but is not intended to be exhaustive or to limit the embodiments to the precise form disclosed. In the preceding description, various embodiments have been described with reference to the accompanying drawings. However, various modifications and changes may be made thereto, and additional embodiments may be implemented, without departing from the broader scope of the invention as set forth in the claims that follow. The description and drawings are accordingly to be regarded as illustrative rather than restrictive.

As set forth in this description and illustrated by the drawings, reference is made to "an exemplary embodiment," "an embodiment," "embodiments," etc., which may include a particular feature, structure or characteristic in connection with an embodiment(s). However, the use of the phrase or term "an embodiment," "embodiments," etc., in various places in the specification does not necessarily refer to all embodiments described, nor does it necessarily refer to the same embodiment, nor are separate or alternative embodiments necessarily mutually exclusive of other embodiment (s). The same applies to the term "implementation," "implementations," etc.

The terms "a," "an," and "the" are intended to be interpreted to include one or more items. Further, the phrase "based on" is intended to be interpreted as "based, at least in part, on," unless explicitly stated otherwise. The term "and/or" is intended to be interpreted to include any and all combinations of one or more of the associated items.

The word "exemplary" is used herein to mean "serving as an example." Any embodiment or implementation described as "exemplary" is not necessarily to be construed as preferred or advantageous over other embodiments or implementations.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

No element, act, or instruction described in the present application should be construed as critical or essential to the embodiments described herein unless explicitly described as such.

What is claimed is:

1. An arm positioning device, comprising:
   a base,
   a wing or panel,
   an arm support mounted on the wing or panel,
   wherein the base has a substantially planar configuration and is configured to be disposed on a support positioned adjacent a therapy or diagnostic apparatus for receipt of a supine patient thereon, wherein the wing or panel is secured to the base and extends upwardly and outwardly therefrom, wherein the wing or panel includes a front planar surface and a rear planar surface, wherein the arm support is configured to hold an upper arm of a patient thereon, whereupon the arm is maintained in an arms-up position, and wherein the arm support is movable between a plurality of working positions located above the front planar surface of the wing or panel on which the arm support is mounted and a retracted position located below the rear planar surface of the wing or panel on which the arm support is mounted so as not to interfere with placement of the patient on the arm positioning device, wherein the wing or panel includes a first plurality of holes provided longitudinally therein, each of which define one of the plurality of working positions for the arm support, and a releasable locking mechanism configured to releasably lock the arm support in any desired one of the plurality of working positions along a longitudinal axis of the base the longitudinal axis, wherein the wing or panel further includes an additional hole spaced apart from the first plurality of holes, wherein said releasable locking mechanism is configured for engagement with the additional hole to hold the arm support in the retracted position.

2. The arm positioning device of claim 1, wherein said wing or panel extends along the longitudinal axis, and wherein the arm support is positionable with respect to the wing or panel on which it is mounted to any of a plurality of positions along said longitudinal axis.

3. The arm positioning device of claim 2, wherein the arm support further comprises a cuff configured to receive of the upper arm of the patient.

4. The arm positioning device of claim 3, wherein the arm support further comprises:
a base member, and
an extension member pivotably mounted with respect to the base member,
wherein the cuff is mounted on the extension member.

5. The arm positioning device of claim 4, wherein the wing or panel comprises:
a channel extending generally longitudinally along the wing or panel,
wherein the base member is positioned within the channel.

6. The arm positioning device of claim 5, wherein the wing or panel comprises a slot that extends within the channel for receiving a portion of the arm support and to define movement of the arm support relative to the wing or panel.

7. The arm positioning device of claim 4, wherein the cuff is pivotably connected to the extension member and configured to be rotated about an axis with respect to the extension member.

8. The arm positioning device of claim 3, wherein the cuff is concave.

9. The arm positioning device of claim 1,
wherein the releasable locking mechanism comprises a spring biased pin for releasable engagement with any one of said first plurality of holes.

10. The arm positioning device of claim 9, wherein said spring bias pin is configured for engagement with the additional hole to hold the arm support in the retracted position.

11. The arm positioning device of claim 9, additionally comprising indicia indicating a longitudinal position of the arm support with respect to the wing or panel on which the arm support is mounted.

12. The arm positioning device of claim 1, wherein the wing or panel comprises a slot that extends generally along the longitudinal axis for receiving a portion of the arm support and to define movement of the arm support relative to the wing or panel.

13. The arm positioning device of claim 12, wherein the wing or panel comprises a forward portion, a rearward portion, an inboard portion and an outboard portion, and wherein the slot is angled inwardly from the outboard portion towards the inboard portion as the slot extends from the forward portion toward the rearward portion.

14. The arm positioning device of claim 1, wherein the arm support is pivotably mounted with respect to the wing or panel on which it is mounted so that the arm support can be pivoted between the working position and the retracted position.

15. The arm positioning device of claim 1, wherein the wing or panel is fixedly secured to said base.

16. The arm positioning device of claim 1, wherein the wing or panel and the arm support comprise a pair of wings or panels, and a corresponding pair of arm supports mounted respectively thereto.

* * * * *

UNITED STATES PATENT AND TRADEMARK OFFICE
CERTIFICATE OF CORRECTION

PATENT NO.         : 10,828,187 B2
APPLICATION NO.    : 15/400457
DATED              : November 10, 2020
INVENTOR(S)        : Roger F. Wilson

Page 1 of 1

It is certified that error appears in the above-identified patent and that said Letters Patent is hereby corrected as shown below:

In the Claims

Column 9, Claim 1, Line 24 should read:
base,

Signed and Sealed this
Twelfth Day of January, 2021

Andrei Iancu
*Director of the United States Patent and Trademark Office*